United States Patent [19]

Takata et al.

[11] 4,026,926

[45] May 31, 1977

[54] PROCESS FOR THE PREPARATION OF METHALLYL SULFONIC ACID AND ITS SALTS

[75] Inventors: Toshihiro Takata; Yoshifumi Kawakatsu; Keitsugu Nohara, all of Shizuoka, Japan

[73] Assignee: Toho Beslon Kabushiki Kaisha, Tokyo, Japan

[22] Filed: July 8, 1975

[21] Appl. No.: 594,019

[30] Foreign Application Priority Data

July 11, 1974 Japan .............................. 49-79420

[52] U.S. Cl. ........................................... 260/513 T
[51] Int. Cl.$^2$ ...................................... C07C 143/16
[58] Field of Search .............................. 260/513 T

[56] References Cited

UNITED STATES PATENTS 3,694,493   9/1972   Lorenz et al. .................. 260/513 T

OTHER PUBLICATIONS

Gilbert, "Sulfonation and Related Reactions," pp. 53–54, 371–373.

*Primary Examiner*—James O. Thomas, Jr.
*Assistant Examiner*—Nicky Chan
*Attorney, Agent, or Firm*—Birch, Stewart, Kolasch and Birch

[57] ABSTRACT

A process for the preparation of methallyl sulfonic acid and its salt which process comprises the reaction of isobutylene with a complex of sulfur trioxide to form methallyl sulfonic acid and, if desired, neutralization of the formed acid with an alkaline compound to obtain its salt. The sulfur trioxide complex is prepared by a reaction of sulfur trioxide with a mono-alkyl substituted amide of an aliphatic carboxylic acid, which has a tertiary carbon atom bonded directly to the nitrogen atom thereof.

5 Claims, No Drawings

PROCESS FOR THE PREPARATION OF METHALLYL SULFONIC ACID AND ITS SALTS

The present invention relates to a process for the preparation of methallyl sulfonic acid and its salts, and more particularly to such process comprising the reaction of isobutylene with a complex of sulfur trioxide.

Methallyl sulfonic acid and its salts are used as the co-monomer to improve the dyeability of acrylic fibers and the like. Hitherto, various processes have been proposed for preparing such useful compounds; among them there is a process comprising the reaction of methallyl chloride with sodium sulfite. According to this conventional method, however, undesirable sodium chloride is simultaneously formed as a by-product. Hence, the yield of the objective compound is considerably lowered owing to difficulty of the isolation from sodium chloride.

In pages 978 and 1594 of J. Am. Chem. Soc. (1941), there is disclosed the reaction of isobutylene with the complex of sulfur trioxide and dioxane to prepare methallyl sulfonic acid. This is also unsatisfactory due to formed by-products which reduce the yield and a low stability of the sulfur trioxide complex of dioxane and thus this process is not suitable for commercial use.

Another process has been proposed for preparing methallyl sulfonic acid without forming undesirable by-products, in which an N, N-dialkyl substituted amide of aliphatic carboxylic acids or an N-alkyl substituted lactam is used as the partner of the sulfur trioxide complex to react with isobutylene. However, when N,N-dimethylformamide (DMF) is used as the typical complex partner, the DMF tends to decompose in the recovery process by distillation, and moreover it is difficult to recover DMF perfectly from the aqueous solution after neutralization of metallyl sulfonic acid with an aqueous solution of an alkaline compound. The remaining DMF discolors the methallyl sulfonic acid.

An object of the present invention is, therefore, to provide a process for preparing methallyl sulfonic acid and its salt, which process can obviate and overcome the disadvantages of the other processes as described above.

A specific object of the present invention is to provide a process to obtain high purity methallyl sulfonic acid and its salt, in a high yield without forming any by-product.

Another object of the present invention is to provide an excellent method of recovering a partner of the sulfur trioxide complex in a high yield from an aqueous solution of methallyl sulfonic acid or its salt.

According to the present invention, the objects as referred to and other objects which will be appreciated by fully understanding the invention can be attained by using a mono-alkyl substituted amide of an aliphatic carboxylic acid, which has a tertiary carbon atom bonded directly to the nitrogen atom thereof, as a compound to form the complex with sulfur trioxide.

As the mono-alkyl substituted amides, N-tert-butylacetamide, N-tert-butylbutyramide, N-tert-butylisobutyramide, N-tert-butylpropionamide, N-tert-butylvaleramide, N-tert-butylacrylamide, N-tert-octylacrylamide, N-tert-dodecylacrylamide and the like may be listed.

The process of the present invention is carried out practically by adding one of said mono-alkyl substituted amides as the complex forming compound in an inert solvent, and sulfur trioxide is added to the resulting mixture in a molar amount approximately equal to that of the mono-alkyl substituted amide at a temperature of between −10° and 20° C and then isobutylene is fed into the resulting complex solution in an equal or a little excess molar amount with respect to the sulfur trioxide.

As the inert solvent which is inert to sulfur trioxide, halogenated hydrocarbons such as methylene chloride, chloroform, carbon tetrachloride, 1,2-dichloroethane, 1,2-dichloropropane or trichloroethylene may be used.

After adding isobutylene, the mixture is gradually heated to react the complex with isobutylene under stirring. The reaction is completed in 2 to 4 hours at a temperature of between 20° and 60° C.

Methallyl sulfonic acid or its salt may be isolated from the resulting solution. Methods for separating the product shall be explained below.

When the mono-alkyl substituted amide used as the complex forming compound is insoluble in water, an aqueous solution of an alkaline compound or water is added to separate the metallyl sulfonic acid or its salt from the complex forming compound. Alternatively, the acid or its salt is separated by distilling off the inert solvent under reduced pressure and then by adding water or an aqueous solution of an alkaline compound from the complex forming compound which is not soluble in water. In the former case, the mixture of inert solvent and the complex forming compound may repeatedly be used, after separation of the aqueous solution of methallyl sulfonic acid or its salt. In the latter case, when the used complex forming compound is not so stable under alkaline conditions, it is preferable to precipitate the complex forming compound by adding water and after separating it the alkaline compound is added. The separated complex forming compound may be reused. As a modification of said latter case, the reaction solution is directly submitted to a preliminary distillation for distilling off a substantial part (about 70%) of the inert solvent, the residue is neutralized by an aqueous solution of alkaline compound, the neutralized solution is distilled under reduced pressure to remove the remaining inert solvent with water and then the residue is filtered to separate the complex forming compound precipitated from the aqueous solution of the desired methallyl sulfonate.

The aqueous solution containing methallyl sulfonic acid or its salt may be isolated, by a conventional manner.

When a water soluble mono-alkyl substituted amide, such as N-tert-butylacetamide is used as the complex forming compound, water is added to the reaction mixture to form an aqueous solution of methallyl sulfonate containing the complex forming compound and then the complex forming compound is extracted with ethyl acetate, amyl acetate or the like.

The invention will now be further definitely explained with reference to examples.

EXAMPLE 1

In a 0.5 liter flask provided with a thermometer, dropping funnel, gas inlet tube, reflux condenser and stirrer, 300g of 1,2-dichloroethane and 32.3g (0.25 mol) of N-tert-butylpropionamide were charged and cooled to −5° C. Thereafter, 23.6g (0.29 mol) of sulfur trioxide was added to the mixture through the dropping funnel. After addition of sulfur trioxide, N-tert-butylpropionamide suspended in 1,2-dichloroethane was converted to a complex to form a colorless transparent solution. The resulting complex solution of sulfur trioxide -N-tert-butylpropionamide was maintained at −5° C and 15.4g (0.275 mol) of gaseous isobutylene was fed into the flask. The resulting mixture was gradually heated under stirring and the stirring was continued for 2 hours at 40° C. The solution was colorless and transparent. The solution was subjected to distillation under reduced pressure (20 mmHg) to remove 1,2-dichloroethane. After distillation of 1,2-dichloroethane, water was added to the residue to precipitate N-tert-butylpropionamide which was filtered and washed well with water. The filtrate was neutralized with an aqueous solution of sodium carbonate. After the neutralization, more of the N-tert-butylpropionamide was precipitated and filtered (recovery rate of N-tert-butylpropionamide: 91%).

The neutralization was carried out with sodium carbonate to pH 7. The neutralized filtrate was evaporated under reduced pressure (20 mmHg) to remove water and to obtain 46.5g of white crystalline sodium methallyl sulfonate. The product was identified with a standard sample by IR spectrum. The purity of the product was 95.5% and the yield 95%.

EXAMPLE 2

The following were obtained by the method as described in Example 1. But N-tert-butylacrylamide and N-tert-octylacrylamide were used as the complex forming compound, respectively, instead of N-tert-butylpropionamide.

| Complex forming compound | N-tert-butyl-acrylamide 32.0g (0.25 mol) | N-tert-octyl-acrylamide 32.8g (0.179 mol) |
|---|---|---|
| 1,2-dichloro-ethane | 300g | 300g |
| Sulfur trioxide | 26.5g (0.331 mol) | 17.6g (0.22 mol) |
| Isobutylene | 20.38g (0.364 mol) | 15.1g (0.27 mol) |
| Sodium methallyl sulfonate | | |
| Yield (g) | 52.4 | 34.4 |
| Yield (%) | 90 | 86.8 |
| Purity | 90 | 88 |

N-tert-butylacrylamide and N-tert-octylacrylamide used as the complex forming compound in this Example could be recovered in an amount of about 95%, respectively.

EXAMPLE 3

In a 0.5 liter flask provided with a thermometer, dropping funnel, gas inlet tube, reflux condenser and stirrer, 297g of 1,2-dichloroethane and 47.2g (0.33 mol) of N-tert-butylisobutyramide were charged and cooled to −5° C. Thereafter, 24.15g (0.3 mol) of sulfur trioxide was added to the mixture through the dropping funnel.

After addition of sulfur trioxide, N-tert-butylisobutyramide suspended in 1,2-dichloroethane was converted to a complex to form a colorless transparent solution. The resulting complex solution of sulfur trioxide -N-tert-butylisobutyramide was maintained at −5° C by cooling the same and 18.55g (0.33 mol) of isobutylene was fed into the flask. And the mixture was gradually heated under stirring and the stirring was continued for 2 hours at 35° C.

The solution was colorless transparent. The solution was submitted to distillation under reduced pressure (20 mmHg) to remove about 70% of 1,2-dichloroethane. The residue containing 1,2-dichloroethane was neutralized with a 20% aqueous solution of sodium hydroxide. The neutralized solution containing the precipitate of N-tert-butylisobutyramide was submitted to distillation under reduced pressure (20 mmHg) to remove the remaining 1,2-dichloroethane with water. After cooling the remaining solution to 5° to 10° C, N-tert-butylisobutyramide was filtered and washed well with water (recovery rate: 93%).

The filtrate was evaporated under reduced pressure (20 mmHg) to remove water and to obtain 47g of white crystalline sodium methallyl sulfonate. By IR spectrum, the product was identified with a standard sample. The purity of the product was 96% and the yield 95%.

EXAMPLE 4

In a flask similar to that as described in Example 1, 300g of 1,2-dichloroethane and 28.7g (0.25 mol) of N-tert-butylacetamide were charged and cooled to −5° C. Then 19.2g (0.24 mol) of sulfur trioxide was added to the mixture through the dropping funnel. N-tert-butylacetamide suspended in 1,2-dichloroethane is converted to a complex with sulfur trioxide, and a colorless transparent solution was obtained. The resulting complex solution of sulfur trioxide -N-tert-butylacetamide was kept at −5° C and 14g (0.25 mol) of isobutylene was fed into the flask.

The solution was gradually heated under stirring and the stirring was continued for 2 hours at 35° C. The resulting solution was colorless and transparent.

Then the solution was submitted to distillation under reduced pressure (20 mmHg) to remove 1,2-dichloroethane. The residue was diluted with water and neutralized with a 20% aqueous solution of sodium hydroxide. The neutralized aqueous solution containing N-tert-butylacetamide and sodium methallyl sulfonate was extracted with 200g of ethyl acetate, to remove N-tert-butylacetamide with ethyl acetate and to leave the sodium methallyl sulfonate in aqueous solution. From the ethyl acetate solution by a usual manner N-tert-butylacetamide was recovered (recovery rate: 90%). The aqueous solution was evaporated under reduced pressure (20 mmHg) to obtain 36g of white crystalline sodium methallyl sulfonate. By IR spectrum, the product was identified with a standard sample. The purity of the product was 95% and the yield 90%.

EXAMPLE 5

The following results were obtained by the method as described in Example 1. But N-tert-butylbutyramide and N-tert-butylvaleramide were used as the complex forming compound, respectively, instead of N-tert-butylpropionamide.

| Complex forming compound | N-tert-butyl-butyramide 35.8g (0.25 mol) | N-tert-butyl-valeramide 39.2g (0.25 mol) |
|---|---|---|
| 1,2-dichloro-ethane | 300g | 300g |
| sulfur trioxide | 19.2g (0.24 mol) | 19.2g (0.24 mol) |
| Isobutylene | 14g (0.25 mol) | 14g (0.25 mol) |
| Sodium methallyl sulfonate | | |
| Yield (g) | 37 | 37.5 |
| Yield (%) | 94.5 | 95.3 |
| Purity | 97 | 96.5 |

N-tert-butylbutyramide and N-tert-butylvaleramide used as the complex forming compound were recovered at recovery rate of 95 and 94%, respectively.

What we claim is:

1. A process for the preparation of methallyl sulfonic acid which comprises adding sulfur trioxide to a halogenated hydrocarbon solution of at least one amide compound selected from the group consisting of N-tert-butylbutyramide, N-tert-butylisobutyramide, N-tert-butylpropionamide, N-tert-butylvaleramide, N-tert-butylacrylamide, N-tert-octylacrylamide, and N-tert-dodecylacrylamide in an approximately equimolar amount with respect to said amide compound at a temperature of between about −10° and 20° C to form a complex thereof, and then adding isobutylene to the resulting complex solution in at least an equimolar amount with respect to the sulfur trioxide at a temperature of between about 20° and 60° C to form the methallyl sulfonic acid.

2. The process of claim 1, wherein said halogenated hydrocarbon is selected from the group consisting of methylene chloride, chloroform, carbon tetrachloride, 1,2-dichloroethane, 1,2-dichloropropane and trichloroethylene.

3. The process of claim 1, wherein the isobutylene and said complex are reacted under stirring.

4. The process of claim 1, further comprising the step of recovering methallyl sulfonic acid from the reaction mixture.

5. The process of claim 4, in which the recovery of the methallyl sulfonic acid is effected by adding water to the reaction mixture, neutralizing said reaction mixture, filtering said reaction mixture and evaporating said filtrate under reduced pressure.

* * * * *